US006975393B2

(12) United States Patent
Mettes (10) Patent No.: US 6,975,393 B2
(45) Date of Patent: Dec. 13, 2005

(54) METHOD AND APPARATUS FOR IMPLEMENTING AN AFTERGLOW EMISSION SPECTROSCOPY MONITOR

(75) Inventor: Jacob Mettes, Boulder, CO (US)

(73) Assignee: Verity Instruments, Inc., Carrollton, TX (US)

( * ) Notice: Subject to any disclaimer, the term of this patent is extended or adjusted under 35 U.S.C. 154(b) by 141 days.

(21) Appl. No.: 10/386,584

(22) Filed: Mar. 11, 2003

(65) Prior Publication Data

US 2004/0179187 A1      Sep. 16, 2004

(51) Int. Cl.$^7$ ............................................. G01J 3/443
(52) U.S. Cl. ...................................... 356/311; 118/715
(58) Field of Search .......................... 356/311, 316, 72, 356/437, 440; 118/715, 724; 438/710; 134/18

(56) References Cited

U.S. PATENT DOCUMENTS

| 5,831,728 A | * | 11/1998 | Malczewski et al. | ....... 356/316 |
| 5,963,336 A | * | 10/1999 | McAndrew et al. | ......... 356/437 |
| 6,105,589 A | * | 8/2000 | Vane | ........................... 134/1.1 |
| 6,197,123 B1 | * | 3/2001 | Poag et al. | ..................... 134/18 |
| 6,279,503 B1 | * | 8/2001 | Choi et al. | ................... 118/715 |

* cited by examiner

Primary Examiner—Layla G. Lauchman
(74) Attorney, Agent, or Firm—Rudolph J. Buchel, Jr.

(57) ABSTRACT

Afterglow spectroscopy allows observing light emission of gaseous species in absence of direct plasma light. This absence avoids the creation of a background spectrum obscuring weak emission from trace species. The invention describes a flowing afterglow version monitoring in-situ the cleanup of vacuum tools during pump/purge cycles. The invention also describes an intermittent afterglow version suitable for trace gas analysis at atmospheric pressure.

121 Claims, 5 Drawing Sheets

METHOD AND APPARATUS FOR IMPLEMENTING AN AFTERGLOW EMISSION SPECTROSCOPY MONITOR

CROSS REFERENCES TO RELATED APPLICATIONS

The present application claims priority from PCT Application No. PCT/US01/28271 entitled "Afterglow Emission Spectroscopy Monitor" filed on Sep. 10, 2001, currently pending, which claims priority from U.S. Provisional Patent Application No. 60/231,588 filed on Sep. 11, 2000 and U.S. Provisional Patent Application No. 60/266,763 filed on Feb. 5, 2001. The above-identified applications are incorporated by reference herein in their entirety.

BACKGROUND OF THE INVENTION

1. Field of the Invention

The present invention relates to semiconductor manufacturing, monitoring of vacuum chamber cleanup and trace gas analysis.

2. Description of Related Art

The semiconductor manufacturing industry achieves higher and higher levels of integration of integrated circuits dealing with contamination and yield problems. Frequent pump/purge cycles with high purity purge gas in between reactive process gas cycles are hereto applied. These pump/purge cycles clean out process gas from a prior reactive process cycle, as well as species like oxygen and moisture that might have entered the tool's chamber. In-situ, real time process monitors of all kind of process variables are considered critical for current and future developments. An example of a new type of monitor is the measurement of trace concentrations of moisture in the exhaust of a semiconductor-manufacturing tool by diode laser based absorption spectroscopy.

Traditionally, monitoring the pressure during pumpdown can reveal gross problems with leaks or excessive outgassing. A pressure gauge, however, is not specific for a particular species. Moreover, most information is in the very tail part of a drydown curve and, in a normal operating procedure, there is simply no time to wait that long. The purge and pump cycles are often done simultaneously, opening wide to the pump while entering a stream of purge gas with a total cycle time in the order of 10 or 20 seconds.

Species specific monitoring can be done with a mass spectrometer that is then called a residual gas analyzer (RGA). Such RGA operates at $10^{-5}$–$10^{-6}$ Torr requiring differential pumping when probing a purge gas at a higher pressure. Mass spectrometers have a residual spectrum at the lower masses that prevents measuring water and oxygen at levels below a part per million.

Some of the above and other in-situ measurement techniques for pump/purge cycles can detect the removal of previously introduced reactive process gas and rare intrusions of excessively high contamination levels. Even to accomplish this limited objective, in-situ techniques, such as RGA, are expensive, maintenance intensive and require elaborate calibration. Moreover, none are sensitive enough and fast enough to follow the actual progress of mentioned 10–20 seconds pump/purge cycles at partial pressures of relevant contaminants in the order of 10–12 atmosphere.

Optical (none afterglow) emission spectroscopy finds practical applications in the semiconductor manufacturing industry. The observation of the spectrum emitted by the process plasma during a process and its evolution over time provides information about the completion of certain reactions such as in end point detection. The presence of a broad background spectrum, however, obscures any weak emission from trace species.

Non-in-situ qualification of cylinder gas or bulk supply of electronic grade nitrogen and argon by metastable transfer emission spectroscopy (MTES) is investigated for oxygen-containing impurities by J. W. Mitchell et al., Analytical Chemistry 1986, 58, 371–374, which is incorporated by reference herein in its entirety. The required bulky and maintenance intensive vacuum technology in such a flowing afterglow application of MTES prevents it from being applied in any practical gas analytical instrumentation.

Non-in-situ gas analysis at parts per billion levels is routinely performed on line for the purge gas prior to its entering into the process tool. At that point, the purge gas is at higher than atmospheric pressure while the analysis can be performed in the order of minutes. The very sensitive and contaminant specific instruments for such purge gas analysis are used downstream of the large purifiers that provide gas to a semiconductor plant's gas distribution manifold. Such instruments are still too complex and expensive to be used as simple end of life detection for point of use purifiers that are used at the purge gas inlet of an individual tool.

Such non-in-situ analysis prior to entering the tool can sometimes also be performed for the reactive process gases although, highly desirable hygrometry of corrosive gases can only be done economically per cylinder, off line, in a laboratory environment.

Even non-in-situ applications requiring only ppm level detection limits can be troubled by the lack of speed, reliability, robustness and ease of maintenance of current state-of-the-art instrumentation. Such applications include a 10-percent increased efficiency of the recovery of argon from an air separation system described in U.S. Pat. No. 4,784,677 entitled "Process and Apparatus for Controlling Argon Column Feedstreams" by Al-Chalabi, and U.S. Pat. No. 5,448,893 entitled "Process for Maximizing the Recovery of Argon From an Air Separation System at High Argon Recovery Rates" by Howard et al., both of which are incorporated by reference herein in their entireties, requiring ideally an analyzer with a one-second response time. U.S. Pat. No. 4,801,209 entitled "Process and Apparatus for Analyzing a Gaseous Mixture and a Visible Emission Spectrum Generator Therefor" by Wadlow, which is incorporated by reference herein in its entirety, describes an analyzer for the maximization of argon recovery, but lacks the robustness and reliability needed for application in a process environment.

SUMMARY OF THE INVENTION

Accordingly, besides the objects and advantages of the monitors described above, several objects and advantages of the present invention are to provide a device and method for sensitive and rapid in-situ gas contaminant monitoring during the pump/purge cycle of vacuum tool equipment where such monitoring includes, among others:

(a) contaminants including oxygen containing species like moisture and molecular oxygen. The device and method according to the invention enables detection at very low levels unattainable by existing prior art technology;

(b) the clean up of reactive process gas introduced prior to the present pump/purge cycle; and (c) the moisture level in reactive process material introduced prior to the present pump/purge cycle.

Other objects and advantages are to provide devices and methods to perform non-in-situ gas analysis in a simple, robust and economical fashion for applications such as end of life detection for gas purifiers and in air distillation applications requiring respectively very low detection limits and very fast response times.

Afterglow spectroscopy allows observation of light emission of gaseous species in the absence of direct plasma light. This absence avoids the creation of a background spectrum obscuring weak emission from trace species. The invention describes a flowing afterglow version monitoring in-situ the cleanup of vacuum tools during pump/purge cycles. The invention also describes an intermittent afterglow version suitable for trace gas analysis at atmospheric pressure.

BRIEF DESCRIPTION OF THE DRAWINGS

The novel features believed characteristic of the present invention are set forth in the appended claims. However, the invention itself as well as a preferred mode of use, further objectives and advantages thereof, will be best understood by reference to the following detailed description of an illustrative embodiment when read in conjunction with the accompanying drawings wherein:

Other features of the present invention will be apparent from the accompanying drawings and from the following detailed description.

DETAILED DESCRIPTION OF THE INVENTION

Figure 1:
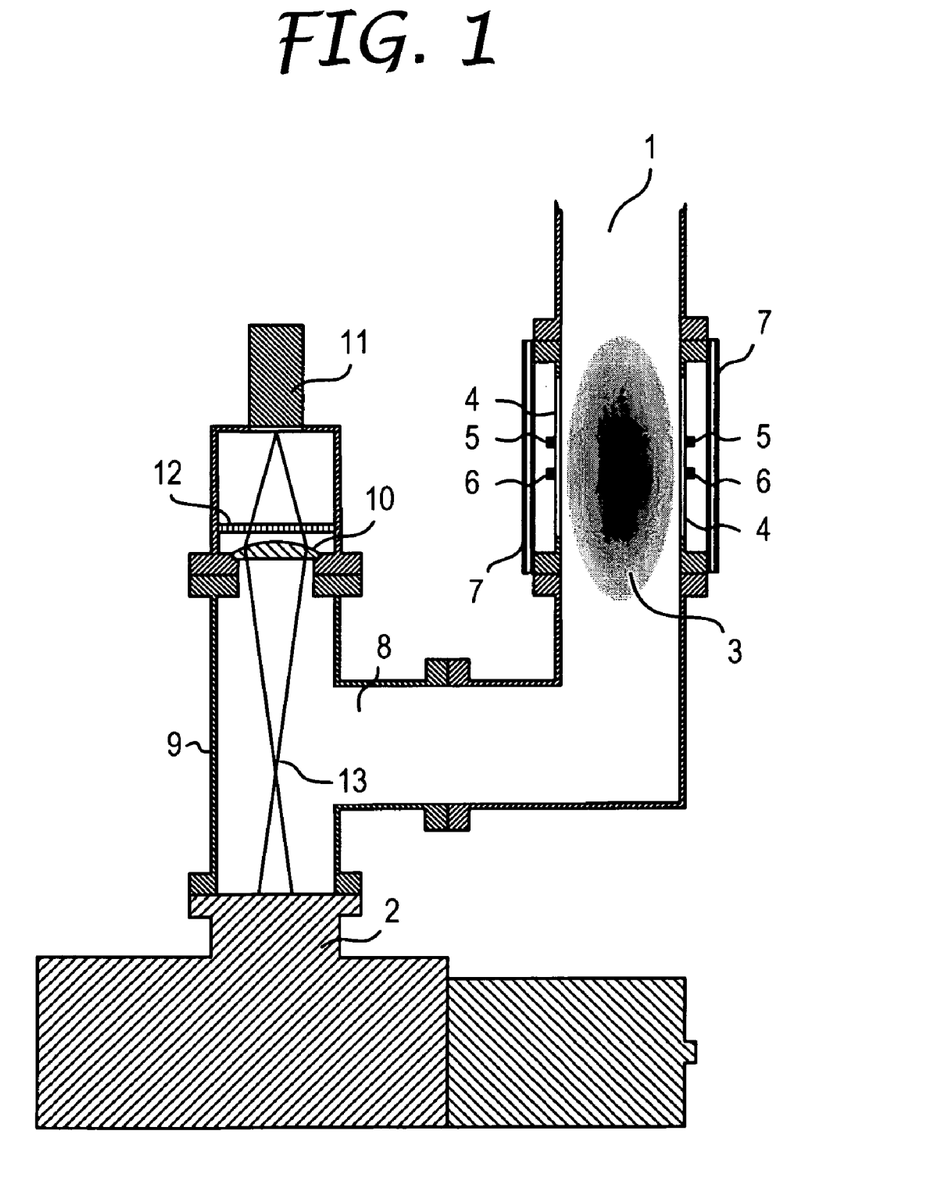
FIG. 1 is a diagram depicting a flowing afterglow monitor with RF plasma excitation on the tool exhaust in accordance with an exemplary embodiment of the present invention.

A first exemplary embodiment of the present invention, depicting afterglow monitor on tool exhaust, is shown in FIG. 1. The afterglow monitor is positioned, e.g., in the gas stream from turbo pump exit 1 of the tool to inlet 2 of the mechanical forepump. The monitor creates its own plasma 3 in a quartz tube 4 equipped with two external circular RF electrodes 5 and 6. The quartz tube 4 conducts mentioned gas stream to the mechanical forepump. Also, shown in FIG. 1 is shield 7 around plasma 3 preventing the device from becoming a source of RF radiation. The plasma 3 will create metastable species that will be taken by the gas flow into central arm 8 of tee piece 9. One of the remaining arms of tee piece 9 connects to inlet 2 of the mechanical forepump, while the other arm features the vacuum tight afterglow observation window/lens 10. This geometry prevents direct plasma light from reaching observation window 10, while lens 10 focuses afterglow emission light on the entrance of a photo multiplier 11. The setup of lens 10 is such that indirect plasma light reflected by the walls is not projected on photo multiplier's 11 entrance. In the presently presented figures, lens 10 and window 10 are shown combined as one single component 10. Interference filter 12 is mounted in between lens 10 and photo multiplier 11 to select the desired emission line wavelength.

More arms can be added to tee piece 9 to observe afterglow emission at additional wavelengths through additional windows and interference filters. The geometry for mounting such additional arms should avoid direct plasma 3 light from reaching the arm's observation window while a lens is used to focus light from the afterglow on the corresponding multiplier.

The inside of aluminum vacuum pieces such as tee 9 can be black anodized to absorb direct plasma light, thus reducing the light reaching the observation window through reflections.

FIG. 1 also shows the use of an additional elbow vacuum piece in between plasma 3 and afterglow observation area 13 to provide an additional barrier for direct plasma light to reach observation window 10.

Quartz tube 4 in between plasma 3 and electrodes 5 and 6 avoids potential contamination from contact of the metal electrodes with the plasma.

Optionally, the first exemplary embodiment of the present invention can, instead of using its own plasma 3 source, use the plasma of the process tool itself. This is achieved by igniting (after an impedance match) the tool's plasma in a purge gas stream of inert gas like nitrogen or argon.

Figure 2:
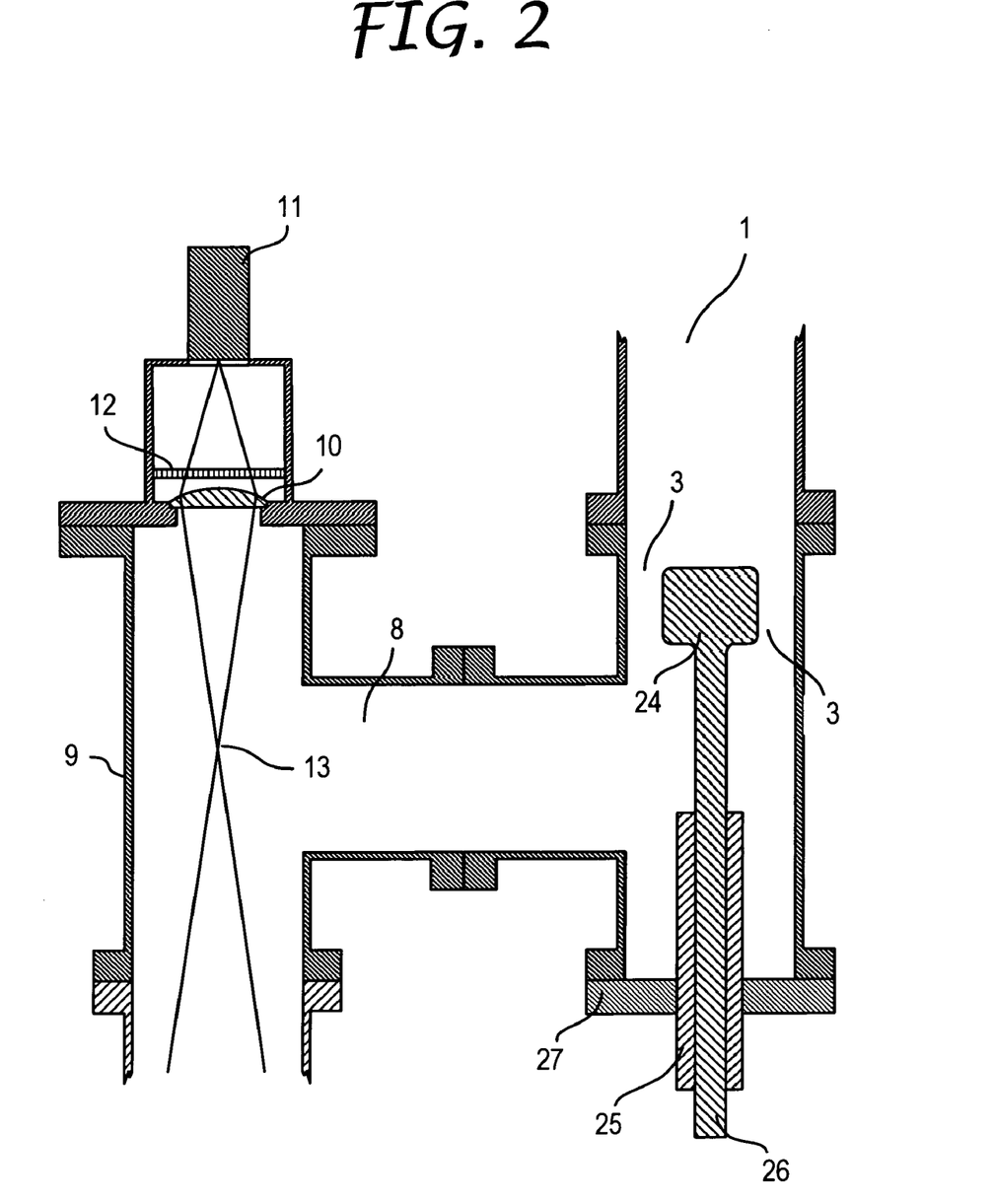
FIG. 2 is a diagram depicting a basic flowing afterglow monitor with DC plasma excitation in accordance with an exemplary embodiment of the present invention.

A second exemplary embodiment of the present invention, depicting afterglow monitor with DC plasma, is shown in FIG. 2, differs from the first exemplary embodiment as far as its plasma source is concerned. Quartz tube 7 and coils 5 and 6 of the RF plasma in FIG. 1 are replaced by center electrode 24 that is connected outside the tool's chamber to a high voltage DC power supply through an electrical feedthrough in flange 27. Connection 26 of the feedthrough is electrically isolated from flange 27 by isolation 25. The walls of the electrically-grounded metal chamber surrounding center electrode 24 form the second electrode. Plasma 3 is now created in between the first, center, electrode 24 and the second electrode being the chamber's wall. The simpler second exemplary embodiment of the present invention is subject to contamination such as evaporating traces of metal generated by the contact of the metal electrodes with the plasma. However, it is unlikely that such traces of metal contamination will emit light downstream of the gas stream as the result of a collision with metastable species. Moreover, the wavelength and width of interference filter 12 can be used to block such unwanted light emission.

Figure 3:
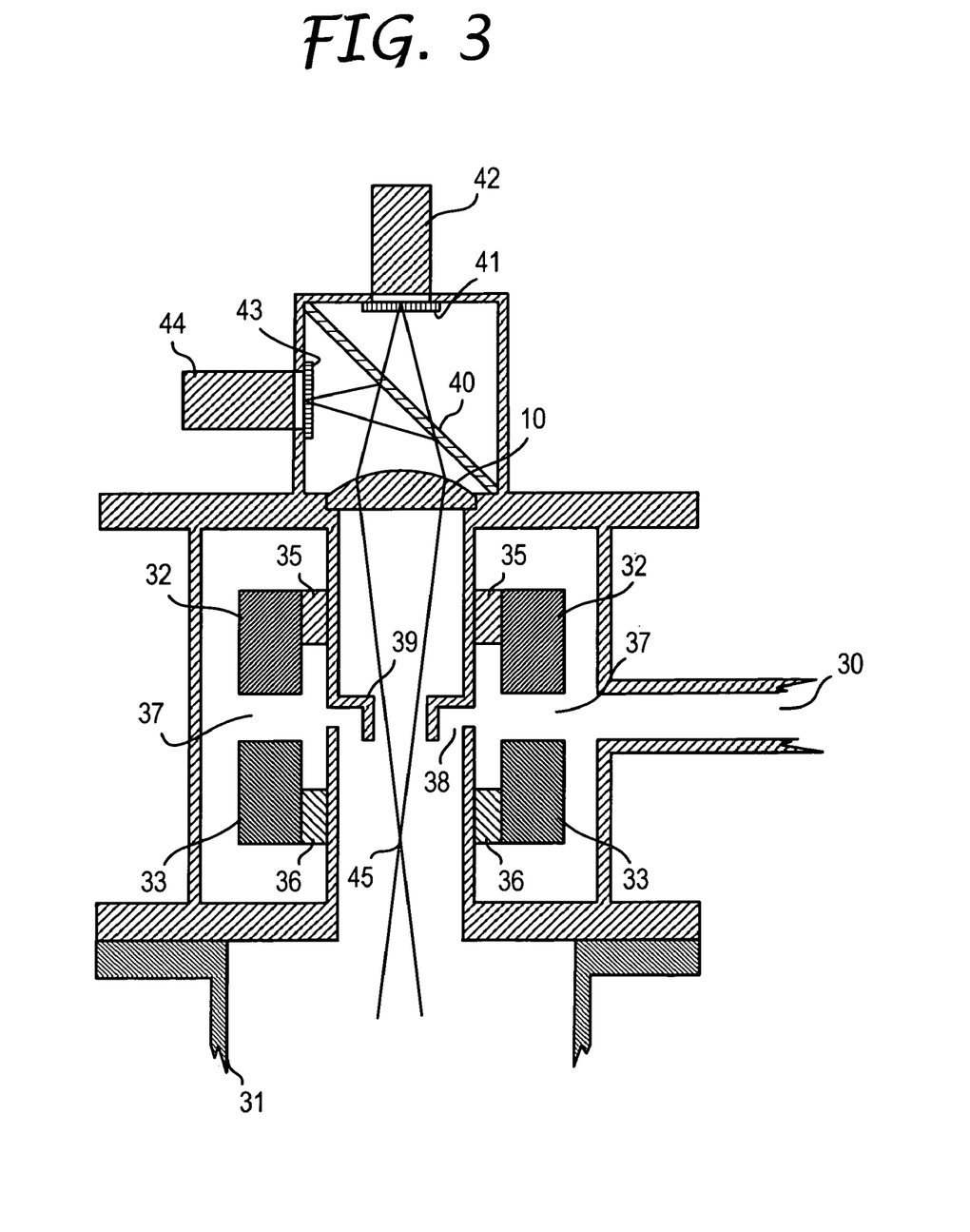
FIG. 3 is a diagram depicting a flowing afterglow monitor at the tool's purge gas inlet in accordance with an exemplary embodiment of the present invention.

A third exemplary embodiment of the present invention, depicting afterglow monitor at the tool's purge gas inlet, is shown in FIG. 3. The afterglow monitor is positioned in between purge gas stream 30 downstream of, e.g., a mass flow controller and flange 31 connecting to the tool's vacuum chamber. Plasma 37 is created in the space between two similarly sized coaxial ring shaped electrodes, 32 and 33, that face each other. Each electrode 32 and 33 is mounted by means of a coaxial ring shaped insulator, respectively, 35 and 36. The gas stream first passes through the space with plasma 37 where after it flows through a ring shaped slot 38 to flow into the tool's vacuum chamber. The afterglow emission is observed through vacuum tight window 10 that is shielded from direct plasma light by the geometry of shield 39 around slot 38. Shield 39 prevents direct plasma light to reach observation window 10 while providing limited wall contact to minimize loss of metastables by wall collisions. Beam splitter 40 enables observation of different wavelengths of afterglow light with multiple interference filter and photo multiplier combinations 41, 42 and 43, 44 using one and the same observation lens/window combination 10.

Besides impurities already present in the purge gas itself, the third exemplary embodiment of the present invention allows observation of species from inside the tool's process vacuum chamber that back diffuse into the stream of metastables that exits the monitor. Such backdiffused species will react with these metastables and resulting light emission can be monitored by the afterglow monitor. These backdiffusing species are the indicators of the quality of the ongoing purge.

Apart from purge gas, also part of the process gas constituents, like argon, can be made to enter the tool passing through the afterglow monitor during reactive process cycles. This will protect the monitor's observation window 10 from process tool plasma deposits that will now have to diffuse against a "counterflow."

Optionally not shown in the FIG. 3, a mechanical shutter, e.g. of the venetian blind type, can be positioned in between the afterglow monitor's process tool connection flange and the mating process tool's connecting flange. This blind can, on the one hand, protect the observation window during active, non-purge, process cycles. On the other hand, during purge cycle monitoring, shutting the blinds can drastically reduce the influx of species backdiffusing from inside the process tool's chamber into the afterglow monitor's observation zone. A venetian blind kind of shutter consists of an array of parallel metal strips that can rotate around their longitudinal axis and are shown as component 70 in another context in FIG. 5. The blind does not shut in a vacuum or leak tight manner at all, but when shut, it will restrict the gas stream somewhat and force it locally into flowing at an increased speed. This speed increase through narrower openings will effectively reduce backdiffusion. This way, shutting the blinds will show the emission spectrum from the purge gas in absence of impurities added by the tool. Such emission spectrum can serve as a reference or zero as it corresponse to the ultimately achievable end result of purging a perfectly cleaned tool, similar to that discussed hereunder in the fourth exemplary embodiment of the present invention. Eventually, an additional L piece can be added in between the venetian blind and the afterglow monitor's connection flange 31 to assure equal observation areas for opened and closed blinds.

Figure 4:
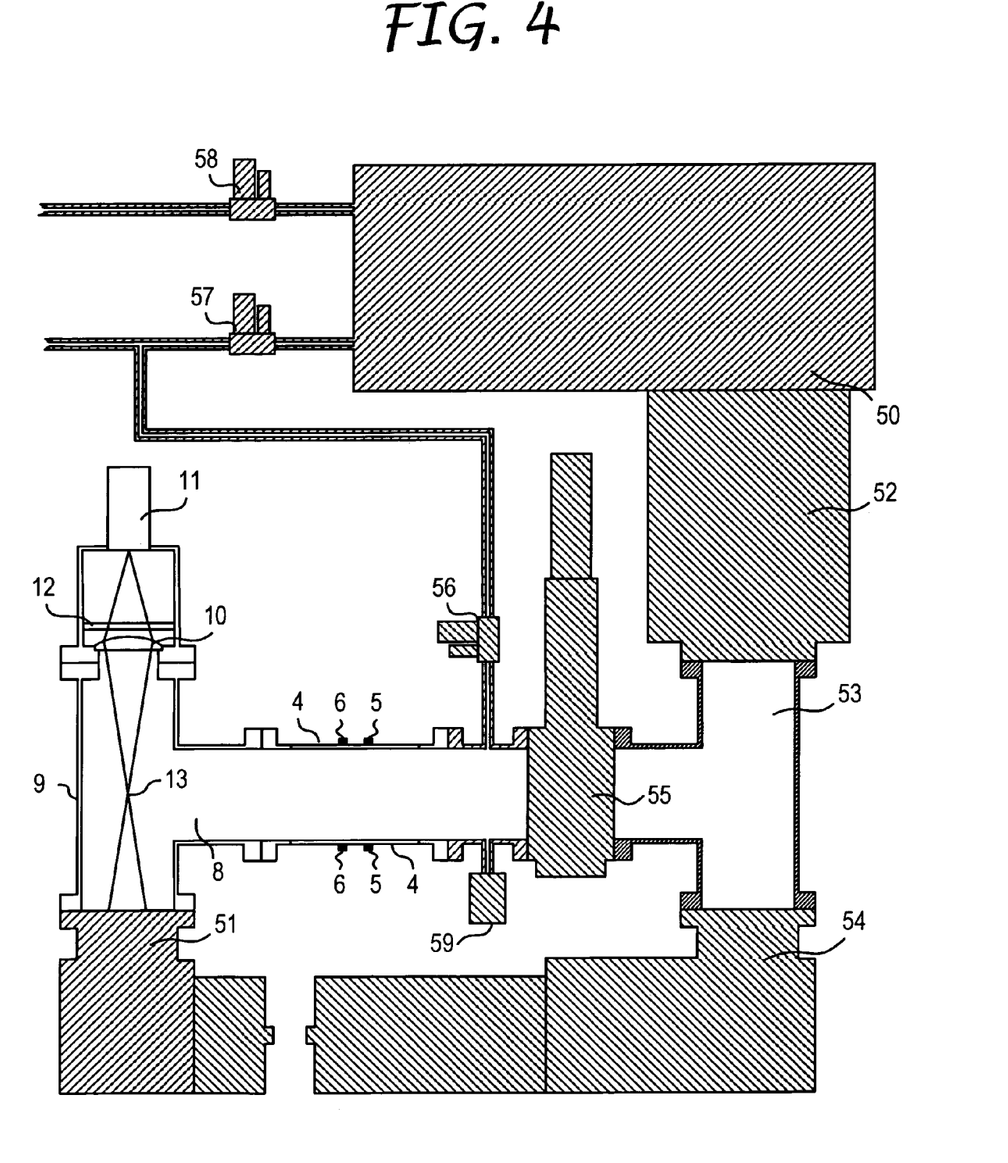
FIG. 4 is a diagram depicting a flowing afterglow monitor with a zero reference in accordance with an exemplary embodiment of the present invention.

A fourth exemplary embodiment of the present invention, depicting afterglow monitor with zero reference, is shown in FIG. 4. This embodiment is basically that of the first exemplary embodiment with added provisions to monitor purge gas that bypassed tool 50, thus providing a zero reference. The zero reference's afterglow emission corresponse with the asymptotically approached ultimate end result of a perfectly purged tool 50. Contributions on top of the zero reference are tool 50 contributions, which can be separated by subtracting the zero reference from a regular tool 50 measurement. Such subtraction can be done most easily for measurements done in the linear part of the calibration curve.

The afterglow monitor in the first exemplary embodiment and the second of the present invention uses the mechanical fore pump from the tool itself. This fourth exemplary embodiment has an afterglow monitor with its own mechanical fore pump 51. A stream of purge gas exiting tool 50 is teed off from the gas stream between the tool's turbo pump 52 exit 53 and the tool's mechanical fore pump 54. Isolation valve 55 can block this teed off stream which is then replaced by a gas stream of purge gas entered directly through a Mass Flow Controller (MFC) 56 in between the afterglow monitor's inlet and isolation valve 55. Purge gas to purge the tool enters through MFC 57, while process gas enters through MFC 58. When the isolation valve 55 is closed, e.g. during active non-purge process cycles, mentioned zero reference can be obtained while a feedback loop tunes MFC 56 to reproduce the same pressure gauge 59 reading that is present during regular purge gas monitoring conditions with isolation valve 55 opened.

In fact, with an opened isolation valve 55 during a tool 50 purge, MFC 56 can be tuned over a range of flowrates while MFC 57 is adapted to maintain a fixed pressure at the indicated pressure gauge 59. This range for MFC 56's flowrate can vary from, on one extreme, a minimum to prevent a stagnant flow at the MFC 56's outlet connection. This corresponds to monitoring undiluted purge gas exiting tool 50. On the other extreme, MFC 56's flowrate can be made large enough to provide not only a flow through the afterglow monitor into the afterglow monitor's mechanical forepump 51, but also an excess flow streaming away from the afterglow monitor mixing in with the purge gas exiting tool 50 toward mechanical forepump 54 of tool 50. This situation would correspond to monitoring undiluted purge gas without contributions from tool 50 that would have to diffuse against the excess purge gas flow. In between these extremes, mixtures of pure purge gas and purge gas with tool contributions can be generated where the ratios can be determined from the MFC 56 flowrate and a measurement of the flowrate at the exit of the afterglow monitor's mechanical forepump 51. Such setup enables to dilute very contaminated purge gas exiting the tool 50 thus assuring measurement on the linear part of the calibration curves. Optionally, this last described setup could function also without isolation valve 55 or with a venetian blind shutter instead of isolation valve 55 to avoid potential contamination during active process cycles.

The isolation valve 55 setup, however, enables a single afterglow monitor with a single corresponding MFC 56 to be connected to several tools of, e.g. a cluster tool, serving one at the time, where each cluster tool has its own isolation valve 55.

Figure 5:
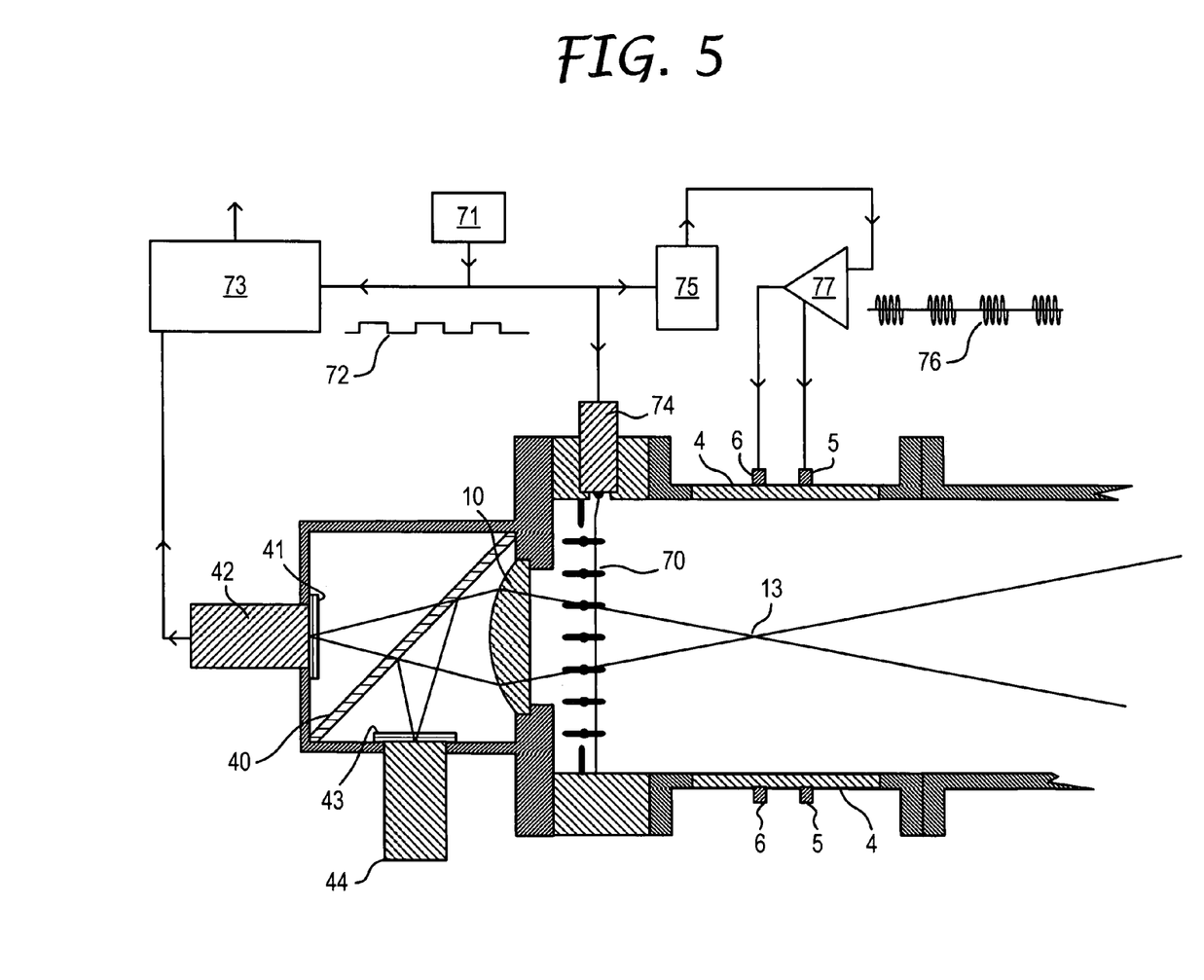
FIG. 5 is a diagram depicting a afterglow monitor with intermittent plasma and lock-in detection in accordance with an exemplary embodiment of the present invention.

Fifth exemplary embodiment of the present invention: intermittent afterglow monitor. FIG. 5 shows the intermittent afterglow setup combined with a phase sensitive, lock in, detection scheme. The mechanical shutter is shown as a venetian blind 70 with activator 74, but can be a perforated rotating wheel, a butterfly structure, etc. In principle, the phase sensitive detection allows measurement of signals smaller than the background signal fluctuations that otherwise set the limit to the achievable detection limit. Hereto, however, shutter 70 created optical isolation from the plasma must be perfect, leaving only dark counts as they signal from photo multiplier 42 (and 44).

A low frequency square wave generator 71's signal 72 is offered to the lock-in 73 as reference signal, while it is also offered to actuator 74 of mechanical shutter 70 and to the amplitude modulation input of a RF signal generator 75. In case of, e.g. a mechanical rotating chopper wheel, such low frequency square wave signal can be taken directly from the chopper and offered to the lock-in's reference input and the RF generator 75's AM input.

RF generator 75 will produce periods of RF signal 76 in phase with the periods of a closed shutter (chopper). RF generator 75's output will be amplified by amplifier 77 and offered to electrodes 5 and 6 of the plasma. Periods of open chopper 70 will result in afterglow signals from the photo multipliers 42.and 44. A closed chopper photo multiplier signal will correspond, as discussed, with the dark count of the multiplier. Lock-in 73 will produce an output signal proportional to the average signal contribution from the afterglow emission during a chopper 70 period.

Alternative methods of data treatment consist of curve fitting a down-going exponential to the signal obtained as a function of time during the individual open chopper periods. Other options would be to ignore the closed shutter signals and produce a signal proportional to the average emission received during the open shutter periods using gated electronics. If the shutter adequately isolates plasma light, one could also output the averaged received light from the photo multiplier(s).

If necessary, any of the described afterglow monitor exemplary embodiments can be isolated from vibrating components such as the mechanical forepump by, e.g., bellows in order to protect more delicate parts such as a photomultiplier.

OPERATION

Background spectrum: Optical plasma emission spectroscopy is typically not suited to measuring trace concentrations of species. Even high-resolution spectroscopy is of limited use in case of trace concentrations because of the presence of a broad background spectrum. The invention is based on the avoidance of this background spectrum made possible by the realization that it is caused mainly by fluorescence of impurities in the (quartz) observation window/lens 10 irradiated by strong main (UV) lines of the plasma. Apart from this fluorescence, the presence of strong plasma lines and possibly other plasma emissions make it also difficult to detect weak signals from trace concentrations in the plasma.

Shielding of the window: The invention shields observation window/lens 10 from direct plasma emission by creating a "dark" area in front of it. This is done, on the one hand, by geometrical shielding with one or more screens blocking a straight path from the plasma to window 10. Additional blackening of the screens and parts of the chamber can be used to reduce plasma (UV) light reaching window 10 after one or more reflections. Additionally, dark zones created in the plasma, e.g., near the electrodes in a DC plasma or with grounded plates, can also be used to limit direct emission from irradiating the window. These forms of shielding are applied for a plasma that is continuously ignited during, for example, purge cycles of a semiconductor manufacturing process, in contrast to the hereafter discussed intermittent plasma.

On the other hand, observation window or lens 10 can be shielded from plasma light by means of mechanical shutter 70 positioned in between window 10 and the plasma. Extinguishing the plasma and opening shutter 70 allows the observation of the afterglow emission decreasing over time. Shutter 70 can be closed again and the plasma reignited whereupon the cycle is repeated. Such intermittent cycles can be repeated many times, e.g., during one semiconductor manufacturing purge cycle. This form of shielding is applied in the invention's intermittent plasma afterglow monitoring.

Afterglow: Long lived high energetic species, such as metastables, created previously in the plasma end up in front of observation window 10 either by travel in case of the flowing afterglow or by the removal of the chopper barrier in case of the intermittent afterglow. In the flowing afterglow mentioned, travel into the invention's shielded "dark" area can take place either by moving with a stream of gas by diffusing into a stagnant flow or even by moving against a stream of gas (back diffusion). The mean free path without collision of a species in a low-pressure environment can become relatively long, while an excited argon atom cannot lose its energy efficiently colliding with another argon.

The afterglow spectrum observed in isolation of the main plasma has a much less complex emission spectrum than the main plasma itself. The dominant mechanism of excitation of an atom or molecular species by high energetic electrons is replaced by recombination and energy transfer by other atoms, ions or molecules. This results in a much less dense matrix gas spectrum where trace impurity emission appears more clearly in absence of mentioned broad background spectrum.

Interpretation of the spectrum: It is typically difficult to extract quantitative information regarding the type and concentrations of contaminating species present prior to their entrance into the plasma from the information regarding the resulting species observed in the plasma. The highly energetic plasma environment decomposes molecular species that recombine into new species. As an illustrative example, a plasma of argon with 2 ppm $H_2$ and 1 ppm $O_2$ will have similar OH emission as a plasma with 2 ppm $H_2O$.

Another difficulty is that quantitative emission spectroscopy not only involves the concentration of emitting species, but also the intensity of the source of excitation. The invention realizes that a plasma created in ultra high purity purge gases, such as argon or nitrogen used in semiconductor manufacturing tools, addresses both difficulties. On the one hand, such gases decompose in a very limited number of fragments while there is only a handful of impurity types. On the other hand, such plasma provides a stable source of excitation little impacted by the presence of the very low trace concentrations of impurities. As a result, calibration curves will be linear at low concentrations.

The invention can use chemometrics to address remaining non-specificity, basically solving n unknown trace concentrations from n, or more, quantified emission line intensities. The presently-described invention can use additional distinguishing characteristics that are presented hereunder.

Additional distinguishing characteristics: Moisture and oxygen are the main contaminants in most semiconductor manufacturing processes and typically have a negative impact on the process yield. Removal of these two impurities is also the main goal of the pump/purge cycles performed in between active process cycles. In contrast to a molecule like oxygen, a moisture molecule is very "sticky" and has a tendency to reside on the walls of a process chamber. This characteristic makes that during an evacuation, or purge, oxygen is removed relatively fast while moisture is removed much slower.

The way impurities such as moisture and oxygen are introduced into the process chamber also results in different behavior. Oxygen is typically introduced as a leak from the atmosphere into the chamber. Moisture typically outgases from chamber components like O-rings or from materials from, e.g., wafer trays, brought into the chamber. This makes a difference in pumpdown speed, there is also a difference in asymptotic value approached during prolonged purging. An oxygen leak will create a non-zero plateau, while moisture will eventually reach zero.

Presented additional distinguishing characteristics allow mathematical treatment of data obtained as a function of time. Such mathematical treatment can be, but is not limited to, checking if higher derivatives approach zero or, e.g., curve fitting with one or more downgoing exponentials, etc.

Indirect detection of wet process gas: Hygrometry in corrosive gasses is typically problematic because it exposes delicate sensor parts to corrosion. The present invention allows for monitoring the wetness of the process gas used in the cycle prior to a purge cycle. Moisture, as a very sticky molecule, entered into the process chamber by, e.g., wet HCl, will stick long enough to the walls of the chamber to be noticeable by afterglow monitoring in the following purge cycle. Means to distinguish such moisture from that of other sources can be: enter process gas without ignition of the process plasma, vary the introduction time or flowrate of the process gas, and differences with and without a stack of wafers present in the tool chamber.

Pump/purge efficiency monitoring: As mentioned, the purpose of the pump/purge cycles in a semiconductor manufacturing process is typically to remove such trace impurities as moisture and oxygen. In absence of real time data regarding the efficiency of an ongoing pump/purge cycle, a tool operator has to rely on prior experimentally determined purge times that proved adequate under most "normal" operating conditions. These purge times will be applied plus an additional safety margin. In situ metrology will not only cut excess purge time that will become available as process time. It will also catch contamination problems as soon as they occur, thus avoiding time and material costs related to the manufacture of unusable product runs. In-situ monitoring can also cut startup time after maintenance and save costs running test wafers.

Even when used only as a qualitative monitor, the invention allows following the evaluation of characteristic emission line intensities during the pump/purge cycle, which provides a measure for the reproducibility of this part of the process. It can also give an indication whether or not further purging is worthwhile.

Calibration: Calibration of the monitor can be done by the introduction of a purge gas with known concentrations of, e.g., oxygen and moisture. A stable flowrate of such gas can be created at various pressures in the range of interest.

Using the linearity of the monitor's response at low concentrations and the absence of a background spectrum, one can also add calibrated concentrations to an unknown purge gas. Extrapolation allows determining the unknown purge gas concentration.

Using the large volume of the tool chamber upstream of the afterglow monitor, exponential dilution can be used to generate a large range of calibrated concentrations as a function of time. Hereto, a known concentration of, e.g., oxygen or moisture, in high purity purge nitrogen, is flowing until stable afterglow emission is reached in an equilibrium situation. Then a switch introducing only a flow of high purity purge gas is made into the tool whereupon the monitored concentration at the outlet of the tool will follow an exponentially down going function of time. This function can be calculated from the volume of the chamber, the initial concentration, and the size of the flowrate of the purge gas.

Window depositions: The transparency of an observation window in a vacuum chamber used to perform active process steps like chemical vapor deposition might degrade over time. Solutions preventing window deposition range from the creation of a counter gas flow away from the window to window shutters and "venetian blinds", to an isolation valve to protect the window during active process cycles.

Compensation for window depositions can be done in the following further described setups that allow creating a zero or reference emission spectrum. This zero or reference spectrum can be used to "normalize" other measurements. Results can be based on the ratio of line intensities and the zero spectrum line intensities, thus compensating for changes in the transparency of the observation window.

Normalization: As previously mentioned, quantitative emission spectroscopy involve not only the concentration of the emitting species, but also the intensity of the source of the excitation. In case there are emission lines available that are a measurement of the intensity of the source of excitation, such lines can be used to "normalize" a quantitative measurement. This allows for correction in fluctuations in the intensity of the source of excitation. An example according to the invention is the use of afterglow emission caused by transitions from $N_2(C^3\Pi_u)$ to $N_2(B^3\Pi_g)$ in a nitrogen plasma. Two $N_2(A^3\Sigma)$ metastable nitrogen molecules can react with each other leaving one of the molecules in the $(C^3\Pi_u)$ state. This makes the concentration of metastable $N_2(A^3\Sigma)$ proportional to the square root of the intensity of mentioned afterglow emission ($N_2(C^3\Pi_u)$ to $N_2(B^3\Pi_g)$).

Metastable production: Plasma conditions such as DC voltage and current or AC frequency, voltage and current can be tuned to generate high concentrations of metastable species in the plasma. Metastables can loose their energy either by wall collisions or by collisions with trace impurities. The rate of losses of metastables through wall collisions depends on the diameter of the tubing, the flowrate of the gas, pressure, diffusion coefficient, concentration of metastables generated in the plasma and the distance downstream of the plasma. Energy loss through collision with trace impurities depends on the concentration of the impurities and the reaction rate. The metastable concentration will be stable at low impurity concentrations resulting in a linear calibration curve. Such curve will eventually flatten at high impurity concentrations that deplete the metastable concentration making less metastables available to generate afterglow emission.

Emission spectra: The afterglow emission is typically generated by highly excited diatomic species which can be molecules or radicals created mostly from recombining fragments of species decomposed in the plasma. The emission spectrum associated with a particular transition between specific molecular states appears in the form of bands containing peaks each associated with a specific vibrational initial and final state. For the purposes of this invention, a particular wavelength has to be selected, e.g., when an interference filter is used. In principle, any major peak, or group of peaks, from a band can be chosen for the monitoring as long as it is not in the vicinity of possible other afterglow emission wavelengths from another species.

Argon purge gas: The metastable state of Argon$^3P_2$ is typically the main source of excitation of the impurity molecules and in a much lesser extent metastable Argon$^3P_0$. Emission that can be seen in an Argon afterglow originate from species like, $N_2(C^3\Pi_u)$–$(B^3\Pi_g)$ and radicals like $OH(A^2\Sigma)$–$(X^2\Pi)$ and $CH(A^2\Delta)$–$(X^2\Pi)$.

As discussed above, the main concern when purging a vacuum tool is the removal of moisture and entered atmospheric components like oxygen. Using ultra high purity Argon as purge gas the afterglow's OH, $N_2$, and eventually NO emission enable to monitor for moisture and air leaks. Leaks from atmospheric air will bring in a fixed well-known ratio of nitrogen and oxygen, making de nitrogen emission a good tracer for the presence of the corresponding oxygen. The NO emission can provide additional information.

Nitrogen purge gas: The $N_2(A^3\Pi)$ metastable is the main source of excitation of NO formed in the nitrogen plasma out of oxygen containing species such as moisture and $O_2$. NO emission is caused by transitions from $NO(A^2\Sigma^+)$ to $NO(X^2\Pi)$. Other emission lines in a nitrogen purge gas can be $OH(A^2\Sigma)$–$(X^2\Pi)$ and $CN(B^2\Sigma)$–$(X^2\Sigma)$. See also the Normalization section.

Bypass the tool: A valve arrangement could send a purge gas stream directly into the afterglow detector bypassing the tool. This allows for comparing the difference in emission from the afterglow with and without the contribution from the tool. Such arrangement can be combined with the use of an isolation valve to protect the afterglow monitor during the actual process cycle. Emission spectra from purge gas bypassing the tool, hereinafter called a zero or reference spectrum, can be obtained during the time periods that an active (non purge) cycle takes place in the tool. In some arrangement (see exemplary embodiment of the present invention), the afterglow plasma can stay on continuously.

Performance: Linear calibration curves were obtained up to the parts per million range, with a darkcount rate of the photomultiplier corresponding to one part per billion (moisture in argon). Interference filters instead of the monochromator used to obtain the above-mentioned sensitivity allow catching a much larger fraction of the emitted light, not only in terms of space angle but also in terms of a wider frequency band. This and an optimized design should easily enable 0.1 ppb detection limits with response times in the order of seconds. In a 2 mBar purge gas, such detection limit represents a partial pressure of $2 \times 10^{-13}$ Bar.

Afterglow monitoring of the removal of reactive species introduced prior to the purge/pump cycle: The first exemplary option to do this is simply monitoring afterglow emission associated with remaining reactive species as a function of time during the purge cycle.

A second exemplary option is to use, in addition to the emission of the first option, also emission related to the concentration of purge gas metastable species such as caused by transitions from $N_2(C^3\Pi_u)$ to $N_2(B^3\Pi_g)$ in a nitrogen plasma. Similarly, as described above (see the Normalization section), this last emission can now also be used to normalize the reactive species related emission.

The third exemplary option is to monitor just the mentioned emission related to the concentration of purge gas metastable species such as caused by transitions from $N_2(C^3\Pi_u)$ to $N_2(B^3\Pi_g)$ in a nitrogen plasma. Apart from losses through wall collisions, the metastable species will lose their energy through quenching. Quenching is caused by metastables colliding with other contamination molecules and with molecules from the remainder of reactive species introduced prior to the purge/pump cycle. The better the reactive species are cleaned out by the purge, the stronger the emission from, e.g., a $N_2(C^3\Pi_u)$ to $N_2(B^3\Pi_g)$ transition. This third exemplary option can result in a very simple device where metastables diffuse out of a shielded plasma area into the observation of a photo sensor with an interference filter.

The fourth exemplary option monitors the same emission as the previous third option, but uses the additional information about the strength of this emission at "zero" gas conditions as a reference. Zero gas conditions can be obtained either from the end state of a previous purge/pump cycle or by the above-described purge gas bypassing the tool.

A fifth exemplary option is to operate the flowing afterglow setup in a pulsed fashion. Such an option would require detection optics that gather emissions over a certain length of the path of the afterglow. Such optics can, for example, consist of a photosensor in the focal point of a lens with the observation direction along the flow path of the afterglow. The "flowing" of the afterglow can, as mentioned above, in its simplest form be caused by diffusion of metastables away from a shielded active plasma zone. Monitoring the dying out in time of any afterglow emission following a plasma pulse will reveal information about the presence of quenching species such as the remainder of previously introduced reactive process gas.

A sixth exemplary option combines the fifth exemplary option with information of dying out characteristics of zero gas species following a plasma pulse. This zero gas information can again be used as a reference corresponding to an ideally cleaned tool.

Intermittent afterglow arrangement: An alternative to the hitherto discussed continuous afterglow arrangements is the intermittent afterglow arrangement. In the intermittent afterglow arrangement, the plasma is alternately ignited and extinguished. During plasma ignition, emission is blocked from reaching the observation window by a chopper provision placed in between the window and the plasma. When the plasma is extinguished, the chopper provision clears access to the window. In this way, afterglow emission can be observed in absence of direct plasma light and in absence of fluorescence of impurities in the observation window.

The plasma is created in a volume in front of the chopper provision and might be sustained during most of the blocking period of the chopper. Losses of metastables by wall collision are limited, while phase sensitive lock-in detection can be applied allowing the measurement of afterglow emissions smaller than the darkcurrent of the photomultiplier.

For in-situ monitoring in a vacuum tool however, the mechanical shutter operates under relatively difficult conditions being placed in a vacuum and exposed to a plasma.

However, the intermittent afterglow using, e.g., a fast enough rotating perforated disk chopper can observe the very short-lived afterglow associated with operation at higher gas pressures such as atmospheric pressure. Such a device can perform non-in-situ gas analysis on gases like argon, nitrogen and hydrogen at pressures around atmospheric pressure making it unnecessary to use any vacuum equipment such as a vacuum tight window, pumps etc. The plasma in this case should be very short lived and can be created just by an arc discharge much like the ignition in a spark plug. The position of the rotating disk chopper will trigger the discharge similar to the way as a car's ignition system is triggered by the proper position of the pistons. The chopper disc and surrounding chamber can be made of metal to act as a Faraday cage blocking potentially perturbing electromagnetic radiation when igniting the discharge.

Application involving long lived excited state species: So far, the presently disclosed afterglow emission resulted mainly from energy transfer from non-emitting metastable species to contamination molecules. The presently-described invention can also utilize emissions from long-lived species created in the plasma. An application according to an exemplary embodiment of the present invention is the detection of traces of nitrogen in a matrix of pure oxygen or a matrix of a mixture of oxygen and argon. Nitrogen and oxygen present in a plasma discharge will lead to the formation of species like excited state nitrogen dioxide. Monitoring characteristic nitrogen dioxide emission in the afterglow will be a measurement for the presence of trace nitrogen.

Similarly, traces of oxygen in a nitrogen matrix can be detected. The above-described high pressure intermittent afterglow, according to the invention, is well suited for applications that can be found in air distillation plants described in U.S. Pat. Nos. 4,784,677 and 5,448,893.

CONCLUSION, RAMIFICATIONS, AND SCOPE OF INVENTION

Thus, the reader will see that the afterglow emission spectroscopy in situ monitor can rapidly determine the status of an ongoing pump/purge cycle in vacuum equipment. It can determine the level of cleanup of previously entered reactive gas, and indicate the wetness of such gas when it was entered. It cannot report only unusual high levels of contaminants in the purge gas, but it is also sensitive enough to monitor the presence of contaminants such as oxygen and moisture at trace levels. This last capability provides the data to a tool operator that the pump/purge cycle is actually removing contaminants at levels that matter, or is taking painfully long to lower the last few insignificant ppb. Distinguishing the last could make purge time safety margins available as process time for the tool, thereby increasing the overall efficiency. The afterglow emission spectroscopy in situ monitor is simple and compatible with the materials used in a high vacuum and plasma environment, while at the same time it is easy to calibrate and maintain.

While the above description contains many specificities, these should not be construed as limitations on the scope of the invention, but rather as an exemplification of one exemplary embodiment of the present invention thereof. Many other variations in operating conditions and applications are possible. For example, an alternative to a spark generated plasma in the atmospheric pressure intermittent afterglow can be a plasma generated by a short high energetic laser pulse concentrated in the focal point of a lens. When the laser beam and the afterglow observation axis are perpendicular to each other, there will be no observation of eventual fluorescence induced in the laser lens.

Accordingly, the scope of the invention should be determined not only by the exemplary embodiment(s) illustrated, but also by the appended claims and their legal equivalents. The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

What is claimed is:

1. A monitor device for monitoring afterglow emission to determine impurities in purge gas used to purge a tool chamber, the monitor device comprising:
    a plasma generating means for generating plasma emission;
    an observation area piece for channeling purge gas, said observation area piece at least partially encompassing an observation area;
    an observation means coupled to the observation area piece for observing the observation area; and
    a shielding means for shielding the observation means from direct plasma emission.

2. A method for monitoring afterglow emission in purge gas used to purge a tool chamber using plasma generating means, comprising:
    purging the tool chamber with a purge gas;
    generating a plasma in the purge gas using the plasma generating means;
    shielding an observation area from the plasma;
    directing the purge gas into the observation area; and
    monitoring afterglow emission in the observation area to determine impurities in the purge gas used to purge a tool chamber.

3. The method as recited in claim 2 above, wherein the tool chamber is one of a vacuum plasma process chamber and a load lock, wherein the purge gas enters the tool chamber as an ultra high purity inert gas comprising one of argon and nitrogen wherein the impurities in the purge gas are molecular species that are potentially damaging for the process performed in the tool chamber that are not intentional purge gas constituents, wherein the afterglow emission comprises light emitted by molecules comprising one OH, NO, CH, CN and $N_2$ from a high energetic excited state which formation involves long lived metastable species formed in a plasma, wherein the method uses plasma generating means from the tool chamber's process, wherein the method uses plasma generating means comprises one of a direct current plasma generator, a radio frequency plasma generator and a microwave discharge plasma generator, and independent from the tool chamber's process, wherein the observation means comprises a hermetically sealed optical window, means to select desired optical emission wavelengths and means to detect the selected wavelengths, said means to detect the selected wavelength compromising one of a monochromator, an interference filter, a Fourier transformed spectrometer and an optoacoustic filter and said means to detect the selected wavelengths compromising a photo multiplier, and one of a photo diode, transistor and light sensitive device, wherein direct plasma emission is light emitted by one of an atom and molecular species excited by high energetic electrons in the plasma.

4. The method as in claim 2 above, the method further comprises:
    generating one of a continuous and intermittent plasma during at least a portion of a purge procedure of the tool chamber while the shielding means is related to a separation in space of the afterglow observation zone and the actual plasma, wherein the afterglow observation area and the actual plasma are identical while the shielding means are present in between the plasma and the afterglow observation means when the plasma is ignited and when the shielding means are removed when the plasma is extinguished.

5. The method as in claim 3, the method further comprises:
    generating one of a continuous and intermittent plasma during at least a portion of a purge procedure of the tool chamber while the shielding means is related to a separation in space of the afterglow observation zone and the actual plasma, wherein the afterglow observation area and the actual plasma are identical while the shielding means are present in between the plasma and the afterglow observation means when the plasma is ignited and when the shielding means are removed when the plasma is extinguished.

6. The method as recited in claim 2 above, comprising:
    obtaining a reference afterglow emission spectrum by monitoring purge gas that has not been into contact with the tool chamber;

utilizing the reference afterglow emission spectrum for compensating regular measurements for changes in the observation means's response function, wherein monitoring during a purge cycle provides information of the wetness of reactive or corrosive process gases entered during the process cycle prior to the monitored purge cycle; and diluting purge gas exiting the tool is with purge gas that bypassed the tool prior to entering the afterglow monitor, thereby reducing the concentrations of impurities to levels, wherein the afterglow monitor responds linearly;

selectively monitoring exhaust streams of multiple tools.

7. The method as recited in claim 3 above, comprising:

obtaining a reference afterglow emission spectrum by monitoring purge gas that has not been into contact with the tool chamber;

utilizing the reference afterglow emission spectrum for compensating regular measurements for changes in the observation means's response function, wherein monitoring during a purge cycle provides information of the wetness of reactive or corrosive process gases entered during the process cycle prior to the monitored purge cycle; and diluting purge gas exiting the tool with purge gas that bypassed the tool prior to entering the afterglow monitor, thereby reducing the concentrations of impurities to levels, wherein the afterglow monitor responds linearly;

selectively monitoring exhaust streams of multiple tools.

8. The method as recited in claim 4 above, comprising:

obtaining a reference afterglow emission spectrum by monitoring purge gas that has not been into contact with the tool chamber;

utilizing the reference afterglow emission spectrum for compensating regular measurements for changes in the observation means's response function, wherein monitoring during a purge cycle provides information of the wetness of reactive or corrosive process gases entered during the process cycle prior to the monitored purge cycle; and diluting purge gas exiting the tool with purge gas that bypassed the tool prior to entering the afterglow monitor, thereby reducing the concentrations of impurities to levels, wherein the afterglow monitor responds linearly;

selectively monitoring exhaust streams of multiple tools.

9. The method as recited in claim 5 above, comprising:

obtaining a reference afterglow emission spectrum by monitoring purge gas that has not been into contact with the tool chamber;

utilizing the reference afterglow emission spectrum for compensating regular wherein monitoring during a purge cycle provides information of the wetness of reactive or corrosive process gases entered during the process cycle prior to the monitored purge cycle; and diluting purge gas exiting the tool with purge gas that bypassed the tool prior to entering the afterglow monitor, thereby reducing the concentrations of impurities to levels, wherein the afterglow monitor responds linearly;

selectively monitoring exhaust streams of multiple tools.

10. The method as recited in claim 2 above, wherein the energy to create the afterglow emision is transferred by metastable species, the method further comprising:

normalizing changes in the concentration of the metastable species by a separate measurement of a part of the afterglow emission that is related to the concentration of the metastable species.

11. The method as recited in claim 3 above, wherein the energy to create the afterglow emision is transferred by metastable species, the method further comprising:

normalizing changes in the concentration of the metastable species by a separate measurement of a part of the afterglow emission that is related to the concentration of the metastable species.

12. The method as recited in claim 4 above, wherein the energy to create the afterglow emision is transferred by metastable species, the method further comprising:

normalizing changes in the concentration of the metastable species by a separate measurement of a part of the afterglow emission that is related to the concentration of the metastable species.

13. The method as recited in claim 5 above, wherein the energy to create the afterglow emision is transferred by metastable species, the method further comprising:

normalizing changes in the concentration of the metastable species by a separate measurement of a part of the afterglow emission that is related to the concentration of the metastable species.

14. The method as recited in claim 6 above, wherein the energy to create the afterglow emision is transferred by metastable species, the method further comprising:

normalizing changes in the concentration of the metastable species by a separate measurement of a part of the afterglow emission that is related to the concentration of the metastable species.

15. The method as recited in claim 7 above, wherein the energy to create the afterglow emision is transferred by metastable species, the method further comprising:

normalizing changes in the concentration of the metastable species by a separate measurement of a part of the afterglow emission that is related to the concentration of the metastable species.

16. The method as recited in claim 8 above, wherein the energy to create the afterglow emision is transferred by metastable species, the method further comprising:

normalizing changes in the concentration of the metastable species by a separate measurement of a part of the afterglow emission that is related to the concentration of the metastable species.

17. The method as recited in claim 9 above, wherein the energy to create the afterglow emision is transferred by metastable species, the method further comprising:

normalizing changes in the concentration of the metastable species by a separate measurement of a part of the afterglow emission that is related to the concentration of the metastable species.

18. The method as recited in claim 10 above, wherein the energy to create the afterglow emision is transferred by metastable species, the method further comprising:

normalizing changes in the concentration of the metastable species by a separate measurement of a part of the afterglow emission that is related to the concentration of the metastable species.

19. The method as recited in claim 2 above, further comprising:

determining a quenching measurement from an amount of impurities introduced prior to the purge gas's introduction; and quenching a portion of the afterglow emission that is related to the concentration of the metastable species.

20. The method as recited in claim 3 above, further comprising:
   determining a quenching measurement from an amount of impurities introduced prior to the purge gas's introduction; and
   quenching a portion of the afterglow emission that is related to the concentration of the metastable species.

21. The method as recited in claim 4 above, further comprising:
   determining a quenching measurement from an amount of impurities introduced prior to the purge gas's introduction; and
   quenching a portion of the afterglow emission that is related to the concentration of the metastable species.

22. The method as recited in claim 5 above, further comprising:
   determining a quenching measurement from an amount of impurities introduced prior to the purge gas's introduction; and
   quenching a portion of the afterglow emission that is related to the concentration of the metastable species.

23. The method as recited in claim 6 above, further comprising:
   determining a quenching measurement from an amount of impurities introduced prior to the purge gas's introduction; and
   quenching a portion of the afterglow emission that is related to the concentration of the metastable species.

24. The method as recited in claim 7 above, further comprising:
   determining a quenching measurement from an amount of impurities introduced prior to the purge gas's introduction; and
   quenching a portion of the afterglow emission that is related to the concentration of the metastable species.

25. The method as recited in claim 8 above, further comprising:
   determining a quenching measurement from an amount of impurities introduced prior to the purge gas's introduction; and
   quenching a portion of the afterglow emission that is related to the concentration of the metastable species.

26. The method as recited in claim 9 above, further comprising:
   determining a quenching measurement from an amount of impurities introduced prior to the purge gas's introduction; and
   quenching a portion of the afterglow emission that is related to the concentration of the metastable species.

27. The method as recited in claim 10 above, further comprising:
   determining a quenching measurement from an amount of impurities introduced prior to the purge gas's introduction; and
   quenching a portion of the afterglow emission that is related to the concentration of the metastable species.

28. The method as recited in claim 11 above, further comprising:
   determining a quenching measurement from an amount of impurities introduced prior to the purge gas's introduction; and
   quenching a portion of the afterglow emission that is related to the concentration of the metastable species.

29. The method as recited in claim 12 above, further comprising:
   determining a quenching measurement from an amount of impurities introduced prior to the purge gas's introduction; and
   quenching a portion of the afterglow emission that is related to the concentration of the metastable species.

30. The method as recited in claim 13 above, further comprising:
   determining a quenching measurement from an amount of impurities introduced prior to the purge gas's introduction; and
   quenching a portion of the afterglow emission that is related to the concentration of the metastable species.

31. The method as recited in claim 14 above, further comprising:
   determining a quenching measurement from an amount of impurities introduced prior to the purge gas's introduction; and
   quenching a portion of the afterglow emission that is related to the concentration of the metastable species.

32. The method as recited in claim 15 above, further comprising:
   determining a quenching measurement from an amount of impurities introduced prior to the purge gas's introduction; and
   quenching a portion of the afterglow emission that is related to the concentration of the metastable species.

33. The method as recited in claim 16 above, further comprising:
   determining a quenching measurement from an amount of impurities introduced prior to the purge gas's introduction; and
   quenching a portion of the afterglow emission that is related to the concentration of the metastable species.

34. The method as recited in claim 17 above, further comprising:
   determining a quenching measurement from an amount of impurities introduced prior to the purge gas's introduction; and
   quenching a portion of the afterglow emission that is related to the concentration of the metastable species.

35. The method as recited in claim 18 above, further comprising:
   determining a quenching measurement from an amount of impurities introduced prior to the purge gas's introduction; and
   quenching a portion of the afterglow emission that is related to the concentration of the metastable species.

36. The method as recited in claim 19 above, further comprising:
   determining a a quenching measurement from an amount of impurities introduced prior to the purge gas's introduction; and
   quenching a portion of the afterglow emission that is related to the concentration of the metastable species.

37. The method as recited in claim 2 above, wherein the purge gas used to purge a tool chamber is straight analyte gas not used to purge a tool chamber and, wherein the method is used to determine impurities present in such analyte gas.

38. The method as recited in claim 3 above, wherein the purge gas used to purge a tool chamber is straight analyte gas not used to purge a tool chamber and, wherein the method is used to determine impurities present in such analyte gas.

39. The method as recited in claim 4 above, wherein the purge gas used to purge a tool chamber is straight analyte gas not used to purge a tool chamber and, wherein the method is used to determine impurities present in such analyte gas.

40. The method as recited in claim 5 above, wherein the purge gas used to purge a tool chamber is straight analyte gas not used to purge a tool chamber and, wherein the method is used to determine impurities present in such analyte gas.

41. The method as recited in claim 6 above, wherein the purge gas used to purge a tool chamber is straight analyte gas not used to purge a tool chamber and, wherein the method is used to determine impurities present in such analyte gas.

42. The method as recited in claim 7 above, wherein the purge gas used to purge a tool chamber is straight analyte gas not used to purge a tool chamber and, wherein the method is used to determine impurities present in such analyte gas.

43. The method as recited in claim 8 above, wherein the purge gas used to purge a tool chamber is straight analyte gas not used to purge a tool chamber and, wherein the method is used to determine impurities present in such analyte gas.

44. The method as recited in claim 9 above, wherein the purge gas used to purge a tool chamber is straight analyte gas not used to purge a tool chamber and, wherein the method is used to determine impurities present in such analyte gas.

45. The method as recited in claim 10 above, wherein the purge gas used to purge a tool chamber is straight analyte gas not used to purge a tool chamber and, wherein the method is used to determine impurities present in such analyte gas.

46. The method as recited in claim 11 above, wherein the purge gas used to purge a tool chamber is straight analyte gas not used to purge a tool chamber and, wherein the method is used to determine impurities present in such analyte gas.

47. The method as recited in claim 12 above, wherein the purge gas used to purge a tool chamber is straight analyte gas not used to purge a tool chamber and, wherein the method is used to determine impurities present in such analyte gas.

48. The method as recited in claim 13 above, wherein the purge gas used to purge a tool chamber is straight analyte gas not used to purge a tool chamber and, wherein the method is used to determine impurities present in such analyte gas.

49. The method as recited in claim 14 above, wherein the purge gas used to purge a tool chamber is straight analyte gas not used to purge a tool chamber and, wherein the method is used to determine impurities present in such analyte gas.

50. The method as recited in claim 15 above, wherein the purge gas used to purge a tool chamber is straight analyte gas not used to purge a tool chamber and, wherein the method is used to determine impurities present in such analyte gas.

51. The method as recited in claim 16 above, wherein the purge gas used to purge a tool chamber is straight analyte gas not used to purge a tool chamber and, wherein the method is used to determine impurities present in such analyte gas.

52. The method as recited in claim 17 above, wherein the purge gas used to purge a tool chamber is straight analyte gas not used to purge a tool chamber and, wherein the method is used to determine impurities present in such analyte gas.

53. The method as recited in claim 18 above, wherein the purge gas used to purge a tool chamber is straight analyte gas not used to purge a tool chamber and, wherein the method is used to determine impurities present in such analyte gas.

54. The method as recited in claim 19 above, wherein the purge gas used to purge a tool chamber is straight analyte gas not used to purge a tool chamber and, wherein the method is used to determine impurities present in such analyte gas.

55. The method as recited in claim 19 above, wherein the purge gas used to purge a tool chamber is straight analyte gas not used to purge a tool chamber and, wherein the method is used to determine impurities present in such analyte gas.

56. The method as recited in claim 21 above, wherein the purge gas used to purge a tool chamber is straight analyte gas not used to purge a tool chamber and, wherein the method is used to determine impurities present in such analyte gas.

57. The method as recited in claim 22 above, wherein the purge gas used to purge a tool chamber is straight analyte gas not used to purge a tool chamber and, wherein the method is used to determine impurities present in such analyte gas.

58. The method as recited in claim 23 above, wherein the purge gas used to purge a tool chamber is straight analyte gas not used to purge a tool chamber and, wherein the method is used to determine impurities present in such analyte gas.

59. The method as recited in claim 24 above, wherein the purge gas used to purge a tool chamber is straight analyte gas not used to purge a tool chamber and, wherein the method is used to determine impurities present in such analyte gas.

60. The method as recited in claim 25 above, wherein the purge gas used to purge a tool chamber is straight analyte gas not used to purge a tool chamber and, wherein the method is used to determine impurities present in such analyte gas.

61. The method as recited in claim 25 above, wherein the purge gas used to purge a tool chamber is straight analyte gas not used to purge a tool chamber and, wherein the method is used to determine impurities present in such analyte gas.

62. The method as recited in claim 27 above, wherein the purge gas used to purge a tool chamber is straight analyte gas not used to purge a tool chamber and, wherein the method is used to determine impurities present in such analyte gas.

63. The method as recited in claim 28 above, wherein the purge gas used to purge a tool chamber is straight analyte gas not used to purge a tool chamber and, wherein the method is used to determine impurities present in such analyte gas.

64. The method as recited in claim 30 above, wherein the purge gas used to purge a tool chamber is straight analyte gas not used to purge a tool chamber and, wherein the method is used to determine impurities present in such analyte gas.

65. The method as recited in claim 30 above, wherein the purge, gas used to purge a tool chamber is straight analyte gas not used to purge a tool chamber and, wherein the method is used to determine impurities present in such analyte gas.

66. The method as recited in claim 31 above, wherein the purge gas used to purge a tool chamber is straight analyte gas not used to purge a tool chamber and, wherein the method is used to determine impurities present in such analyte gas.

67. The method as recited in claim 32 above, wherein the purge gas used to purge a tool chamber is straight analyte gas not used to purge a tool chamber and, wherein the method is used to determine impurities present in such analyte gas.

68. The method as recited in claim 33 above, wherein the purge gas used to purge a tool chamber is straight analyte gas not used to purge a tool chamber and, wherein the method is used to determine impurities present in such analyte gas.

69. The method as recited in claim 34 above, wherein the purge gas used to purge a tool chamber is straight analyte gas not used to purge a tool chamber and, wherein the method is used to determine impurities present in such analyte gas.

70. The method as recited in claim 35 above, wherein the purge gas used to purge a tool chamber is straight analyte gas not used to purge a tool chamber and, wherein the method is used to determine impurities present in such analyte gas.

71. The method as recited in claim 36 above, wherein the purge gas used to purge a tool chamber is straight analyte gas not used to purge a tool chamber and, wherein the method is used to determine impurities present in such analyte gas.

72. The method as recited claim 71 above, wherein the analyte gas is the outlet gas of a purifier and the method is used as an end of life detector for the purifier.

73. The device as recited in claim 1 above, wherein the plasma generating means is one of independent of and integral to a process related to the tool chamber and the observation means further comprises:
a hermetically sealed optical window;
a means for selecting a desired optical emission wavelength; and
a means for detecting the selected wavelength.

74. The device as in recited in claim 1 above, wherein the plasma generating means continuously generates plasma during at least a portion a purge procedure for the tool chamber.

75. The device as in recited in claim 1 above, wherein the plasma generating means intermittently generates plasma during at least a portion a purge procedure for the tool chamber.

76. The device as in recited in claim 1 above, wherein the shielding means further comprises:
a vacuum piece coupled between the observation area piece and the tool chamber for channeling purge gas from the tool chamber and into the observation area piece, and for providing spatial separation between the observation means and the plasma generating means for shielding the observation area of the observation means from the direct plasma emission.

77. The device as in recited in claim 76 above, wherein the vacuum piece of the shielding means further comprises:
at least one connection for coupling the vacuum piece to the observation area piece for channeling purge gas from the vacuum piece and into the observation area piece.

78. The device as in recited in claim 77 above, wherein a longitudinal axis of the vacuum piece being non-parallel to an observation axis of the observation means for providing an additional barrier between the direct plasma emission and the observation means.

79. The device as in recited in claim 78 above, wherein the vacuum piece and the observation area piece form a T-connection.

80. The device as in recited in claim 79 above, wherein the observation means further comprises:
a hermetically sealed optical window;
a means for selecting a desired optical emission wavelength; and
means for detecting the selected wavelength.

81. The device as in recited in claim 80 above, wherein the hermetically sealed optical window further comprises an optical lens, and the means for selecting a desired optical emission wavelength further comprise an optical filter; and means for detecting the selected wavelength further comprises at least one detector and at lest one corresponding photo multiplier.

82. The device as in recited in claim 81 above, wherein the observation means further comprises:
a beam splitter; and
a second means for detecting the selected wavelength.

83. The device as in recited in claim 79 above, wherein the plasma generating means further comprises:
at least one electrode disposed within said vacuum piece for generating direct plasma emission.

84. The device as in recited in claim 79 above, wherein the plasma generating means further comprises:
a tool chamber plasma generator for generating direct plasma emission for the tool chamber's process.

85. The device as recited in claim 78 above further comprises:
an afterglow forepump connected to the observation area piece;
an isolation valve coupled between the tool chamber and the vacuum piece for preventing purge gas from entering the vacuum piece from the tool chamber;
a pressure gauge connected to the vacuum piece for monitoring the pressure in the vacuum piece;
a purge gas bypass coupled to the observation area piece for channeling purge gas a directly to the vacuum piece and bypassing the tool chamber; and
a flow controller coupled to the purge gas bypass for controlling the flow of purge gas entering the vacuum piece.

86. The device as recited in claim 85 above further comprises:
a pump connected between the isolation valve and the tool chamber;
an purge forepump connected to the pump and the isolation;
a purge gas port connected to the tool chamber for purging the tool chamber with purge gas;
a second flow controller coupled to the purge gas port for controlling the flow of purge gas entering the tool chamber;
a process gas port connected to the tool; and
a third flow controller coupled to the process gas port for controlling the flow of process gas entering the tool chamber.

87. The device as in recited in claim 1 above, wherein the shielding means further comprises:
a slot in a wall of the observation area piece between the observation means and the plasma generating means for channeling purge gas into the observation area piece; and
a shield portion between the slot and the observation means, said shield portion having a shield body delimited by a first lateral extent, said first lateral extent of the shield portion being proximate a wall of the observation area piece with said shield body extending into the interior of the observation area piece.

88. The device as in recited in claim 87 above, wherein the wall of the observation area piece further comprises a generally cylindrical shape, and the slot defines a generally circumferential opening in at least a portion of a circumference of the cylindrical shaped wall.

89. The device as in recited in claim 88 above, wherein the shield body extends laterally between the cylindrical shaped wall and the observation area.

90. The device as in recited in claim 89 above, wherein the shield body is generally circularly shaped and further comprises:
an orifice for accepting the observation area.

91. The device as in recited in claim 90 above further comprises:
a circularly shaped vacuum piece surrounding the circularly shaped wall of the observation area piece for channeling purge gas through the slot and into the observation area piece.

92. The device as in recited in claim 91 above, wherein the plasma generating means further comprises:
at least one electrode disposed between the exterior of the circularly shaped wall and within the circularly shaped vacuum piece.

93. The device as in recited in claim 91 above, wherein the observation means further comprises:
   a hermetically sealed optical window;
   a means for selecting a desired optical emission wavelength; and
   a means for detecting the selected wavelength.

94. The device as in recited in claim 93 above, wherein the hermetically sealed optical window further comprises an optical lens, and the means for selecting a desired optical emission wavelength further comprise an optical filter; and means for detecting the selected wavelength further comprises at least one detector and at lest one corresponding photo multiplier.

95. The device as in recited in claim 94 above, wherein the observation means further comprises:
   a beam splitter; and
   a second means for detecting the selected wavelength.

96. The device as recited in claim 90 above further comprises:
   a purge gas bypass coupling the observation area piece for channeling purge gas directly to a bypass purge gas stream prior to entering the tool chamber.

97. The device as in recited in claim 1 above, wherein the shielding, means further comprises:
   a mechanical shutter between the observation means and the observation area.

98. The device as in recited in claim 97 further comprises:
   an actuator connected to the mechanical shutter for opening and closing the mechanical shutter.

99. The device as in recited in claim 98 above, wherein the mechanical shutter further comprises:
   a plurality of louvered blinds, each of the plurality of louvered blinds being connected to the actuator.

100. The device as in recited in claim 98 above further comprises:
   a control circuit being electrically coupled to the actuator, said control circuit comprising:
      a signal generator for generating an control signal for controlling said actuator for opening and closing the mechanical shutter.

101. The device as in recited in claim 99 above, wherein the plasma generating means further comprises:
   at least one electrode for generating direct plasma emission.

102. The device as in recited in claim 101 above, wherein the control circuit being further electrically coupled to the at least one electrode and the control signal further controls the at least one electrode for generating the direct plasma emission.

103. The device as in recited in claim 102 above, wherein the control circuit being further electrically coupled to the observation means and the control signal further controls data transmission from the observation means.

104. The device as in recited in claim 103 above, wherein the control circuit being electrically coupled to the observation means for controlling data from the observation means.

105. The device as in recited in claim 1 above, wherein the plasma generating means is one of a direct current plasma generator, a radio frequency plasma generator and a microwave discharge plasma generator.

106. The device as in recited in claim 112 above, wherein the means for detecting the selected wavelength is one of a photo diode, a transistor, an optical sensor and a light sensitive device.

107. The device as in recited in claim 80 above, wherein the means for detecting the selected wavelength is one of a photo diode, a transistor, an optical sensor and a light sensitive device.

108. The device as in recited in claim 93 above, wherein the means for detecting the selected wavelength is one of a photo diode, a transistor, an optical sensor and a light sensitive device.

109. The device as in recited in claim 112 above, wherein the means for selecting a desired optical emission wavelength is one a monochromator, an interference filter, a Fourier transformed spectrometer and an optoacoustic filter.

110. The device as in recited in claim 80 above, wherein the means for selecting a desired optical emission wavelength is one a monochromator, an interference filter, a Fourier transformed spectrometer and an optoacoustic filter.

111. The device as in recited in claim 93 above, wherein the means for selecting a desired optical emission wavelength is one a monochromator, an interference filter, a Fourier transformed spectrometer and an optoacoustic filter.

112. The device as recited claim 100 above, wherein the afterglow emission comes from excited state nitrogen dioxide created in the plasma and either the analyte gas is a mixture containing oxygen in which case the impurities are nitrogen or the analyte gas is a mixture containing nitrogen in which case the impurities are oxygen.

113. A method for monitoring afterglow emission from a tool chamber comprising:
   purging the tool chamber with a purge gas;
   generating a plasma in the purge gas;
   directing the purge gas into an observation area;
   shielding the observation area from the plasma; and
   monitoring afterglow emission in the observation area to determine impurities in purge gas used to purge a tool chamber.

114. The method as recited in claim 113 above, wherein generating a
   plasma in the purge gas further comprises:
   generating the plasma external to the tool chamber.

115. The method as recited in claim 113 above, wherein generating a
   plasma in the purge gas further comprises:
   generating the plasma using a plasma generator for the tool chamber.

116. The method as recited in claim 113 above, wherein generating a
   continuous plasma further comprises:
   exciting the purge gas in a continuous manner.

117. The method as recited in claim 116 above, wherein monitoring afterglow emission further comprises:
   continually sampling the afterglow emission.

118. The method as recited in claim 113 above, wherein generating a
   continuous plasma further comprises:
   exciting the purge gas in a non-continuous manner.

119. The method as recited in claim 118 above, wherein monitoring afterglow emission further comprises:
   sampling the afterglow emission simultaneously with exciting the purge gas.

120. The method as recited in claim 113 above, further comprises:
   determining impurities in the purge gas, comprising:
      bypassing the tool chamber with the purge gas;

generating a plasma in the purge gas;
directing the purge gas into an observation area;
shielding the observation area from the plasma;
monitoring afterglow emission in the observation area; and
a determining an amount of afterglow emission due to impurities in purge gas.

121. The method as recited in claim 120 above, further comprises:
  quenching a portion of the afterglow emission based on the amount of afterglow emission due to impurities in purge gas.

* * * * *